(12) United States Patent
Roy et al.

(10) Patent No.: US 11,364,234 B2
(45) Date of Patent: Jun. 21, 2022

(54) COMPOUNDS AND METHODS FOR TREATING NEMATODE INFECTIONS

(71) Applicants: The Governing Council of The University of Toronto, Toronto (CA); Ontario Institute for Cancer Research (OICR), Toronto (CA)

(72) Inventors: Peter Roy, Toronto (CA); Sean Harrington, Toronto (CA); Jacob Pyche, Peterborough (CA); Daniel Kulke, Monheim (DE); Genna M. Luciani, Toronto (CA); Andrew Burns, Toronto (CA); Mark Lautens, Toronto (CA); Rachel Ross, Toronto (CA); David Uehling, Toronto (CA)

(73) Assignees: The Governing Council of the University of Toronto, Toronto (CA); Ontario Institute for Cancer Research (OICR), Toronto (CA)

( * ) Notice: Subject to any disclaimer, the term of this patent is extended or adjusted under 35 U.S.C. 154(b) by 0 days.

(21) Appl. No.: 16/565,917

(22) Filed: Sep. 10, 2019

(65) Prior Publication Data

US 2020/0078357 A1    Mar. 12, 2020

Related U.S. Application Data

(60) Provisional application No. 62/730,286, filed on Sep. 12, 2018.

(51) Int. Cl.
| | | |
|---|---|---|
| *A61K 31/495* | (2006.01) | |
| *A01N 43/60* | (2006.01) | |
| *A61P 33/10* | (2006.01) | |
| *A61K 31/445* | (2006.01) | |

(52) U.S. Cl.
CPC ............ *A61K 31/495* (2013.01); *A01N 43/60* (2013.01); *A61K 31/445* (2013.01); *A61P 33/10* (2018.01)

(58) Field of Classification Search
CPC .... A61K 31/495; A61K 31/445; A01N 43/60; A01N 43/40; A23K 20/137; A23K 20/116; A61P 33/10
USPC ....................................................... 544/392
See application file for complete search history.

(56) References Cited

U.S. PATENT DOCUMENTS

| | | |
|---|---|---|
| 9,096,608 B2 | 8/2015 | Eickhoff et al. |
| 9,567,345 B2 | 2/2017 | Eickhoff et al. |
| 9,714,219 B2 | 7/2017 | Gauvry et al. |
| 2011/0160054 A1 | 6/2011 | Breuningger et al. |
| 2017/0267657 A1 | 9/2017 | Buysse et al. |
| 2020/0405710 A1* | 12/2020 | Roy ..................... A61K 9/0019 |

FOREIGN PATENT DOCUMENTS

| | | |
|---|---|---|
| EP | 3042645 A1 | 7/2016 |
| JP | 4716672 B2 | 7/2011 |
| JP | 2015131815 A | 7/2015 |
| WO | 2001054507 A1 | 8/2001 |
| WO | 2003088970 A2 | 10/2003 |
| WO | 2005115146 A1 | 12/2005 |
| WO | 2015179414 A1 | 11/2015 |
| WO | 2019147893 A1 | 8/2019 |

OTHER PUBLICATIONS

Artal-Sanz et al . Biotechnol. J. 2006, 1, 1405-1418.*
International Search Report and Written Opinion of corresponding International Patent Application No. PCT/CA2019/051271 dated Jan. 16, 2020, 14 pages.
Fukushi et al., Liquid crystal-related compound-induced cell growth suppression and apoptosis in the chronic myelogenous leukemia K562 cell line, Invest New Drugs, 2011, vol. 29, pp. 827-832.
Burns et al., Caenorhabditis elegans is a useful model for anthelmintic discovery, Nature Communications, 2015, vol. 6, pp. 7485.
Akter et al., Block copolymer micelles for controlled delivery of glycolytic enzyme inhibitors, Pharm. Res., 2012, vol. 29, pp. 847-855.
Beg et al., Synthesis of 1-(N-substituted-carboxamido-2-aminophenyl)-4-methyl-piperazines: D.E.C. analogs and their antifilarial activity-II. Asian Journal of Chemistry, 15 (3), 2003, 1343-1346.
Sanchez-Alonso et al., Piperazine derivatives of benzimidazole as potential anthelmintics. Part 1: Synthesis and activity of methyl 5-(4-substituted piperazin-1-yl)benzimidazole-2-carbamates, Pharmazie, vol. 44 (9) p. 606-7 (Abstract only).

(Continued)

*Primary Examiner* — Irina Neagu
(74) *Attorney, Agent, or Firm* — Bereskin & Parr LLP, S.E.N.C.R.L., s.r.l.; Patricia Folkins (57) ABSTRACT

The present application relates to the treatment of nematode infections. For example, the application relates to the use of compounds of Formula I and/or II as defined herein for treatment of a nematode infection or a disease, disorder or condition arising from a nematode infection:

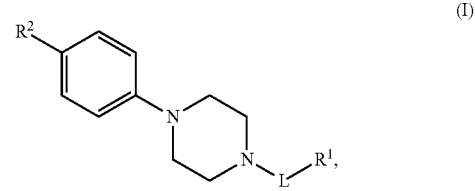

(I)

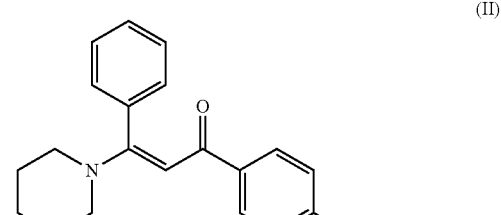

(II)

20 Claims, 2 Drawing Sheets

(56) References Cited

OTHER PUBLICATIONS

Vejdelek and Protiva, 1-(4-Cyclopentylphenyl)piperazine and its 4-substituted derivatives; synthesis and biological screening, Collection of Czechoslovak Chemical Communications, vol. 52, Issue: 7, pp. 1834-1840, 1987 (Abstract only).

Rastogi et al. Synthesis of N-(2-substituted-ethyl)-N'-arylpiperazines and their quaternary salts as potential antihookworm agents, Indian Journal of Chemistry, Section B: Organic Chemistry Including Medicinal Chemistry, vol. 19B, Issue: 11, pp. 1003-1005, 1980 (SciFinder Abstract only).

Husain et al., Search for potent anthelmintics. V. Synthesis of N-arylidene-p-(4-methyl-1-piperazino)anilines, Indian Journal of Chemistry, vol. 13, Issue: 11, pp. 1238-1239, , 1975, (SciFinder Abstract only).

Ye et al. 18F-Labeled benzylpiperazine derivatives as highly selective ligands for imaging s1 receptor with positron emission tomography, Journal of Labelled Compounds and Radiopharmaceuticals (2019), 62(8), 425-437) (SciFinder abstract only).

Ishiwa et al. Evaluation of (+)-p-[11 C]methylvesamicol for mapping sigmal receptors: a comparison with [11C] SA4503' Nuclear Medicine and Biology, vol. 33, Issue: 4, pp. 543-548 (SciFinder Abstract only).

Pyche et al., The Characterization of Molecule 117, a Novel Small Molecule Tool that Likely Inhibits the Vesicular Acetycholine Transporter, 3rd Annual Donnelly Centre Retreat, May 9-10, 2019, University of Toronto, Niagara-on0the Take. Poster.

Pyche et al., The Identification of a Novel Small Molecule Modulator of Acetylcholine Signaling, 2nd Annual, Donnelly Centre Retreat, May 10-11, 2018, Abstract.

Pyche et al., Wact-45 is a Novel Neuromodulator with Anthelmintic Potential, Visions of Pharmacology, 2nd Annual Visions in Pharmacology Research Day, University of Toronto, Toronto, Ontario, Jun. 5, 2018, Abstract.

Harrington et al., A Pipeline for the Discovery of Novel Neuroactive Small Molecule Tools and Candidate Anthelmintics, 2nd Annual Donnelly Centre for Cellular and Biomolecular Research Retreat, May 10, 2018, Abstract.

Harrington et al., A Pipeline for the Discovery of Novel Neuroactive Small Molecule Tools and Candidate Anthelmintics, 2018 Visions in Pharmacology Research Day, Jun. 15, 2018, Abstract.

Pyche et al., Exploiting Locomotor Phenotypes for the Characterization of Novel Neuroactive Compounds in C. elegans, University of Toronto, 2nd Annual Donnelly Centre Retreat, May 18, 2018, Poster.

Pyche J, Discovery and Characterization of wact-45: A novel Acetylcholine Signaling Antagonist. MSc Student seminar, Oct. 23, 2018, Abstract and/or slides not available. Information disclosed includes the Wact-45 compound structure and name.

Harrington et al., Characterizing Novel Inhibitors of Neuromuscular function that may arrest worm infections, University of Toronto, 2nd Annual Donnelly Centre Retreat, May 10, 2018, Presentation.

Harrington et al., A Pipeline for the Discovery of Novel Neuroactive Small Molecule Tools and Candidate Anthelmintics, Satellite Meeting at the CSDB, Mt. Tremblant, Quebec, Mar. 18-19, 2018, Poster.

Driscoll, Monica et al., "Genetic and Molecular Analysis of a Caenorhabditis Elegans B-Tubulin That Conveys Benzimidazole Sensitivity", The Journal of Cell Biology, vol. 109 (No. 6. Pt.1), Dec. 1989, 2993-3003.

Kamisky, Ronald et al., "A New Class of Anthelmintics Effecive Against Drug-Resistant Nematodes", Nature, vol. 452, Mar. 13, 2008, 176-181.

Dent, Joseph A. et al., "The Genetics of Ivermectin Resistance in Caenorhabditis Elegans", PNAS, Mar. 14, 2000, vol. 97, No. 6, 2674-2679.

Fleming, John T. et al., "Caenorhabditis Elegans Levamisole Resistance Genes lev-1, unc-29, and unc-38 Encode Functional Nicotinic Acetylcholine Receptor Subunits", The Journal of Neuroscience, Aug. 1, 1997, 17(15), 5843-5857.

Alfonso, Aixa et al., "The Caenorhabditis Elegans unc-17 Gene: A Putative Vesicular Acetylcholine Transporter", Science, vol. 261, Jul. 30, 1993, 617-619.

Sluder, Ann et al., "Spiroindolines Identify the Vesicular Acetylcholine Transporter as a Novel Target for Insecticide Action", PLOS One, May 1, 2012.

* cited by examiner

COMPOUNDS AND METHODS FOR TREATING NEMATODE INFECTIONS

RELATED APPLICATIONS

The present application claims the benefit of priority of U.S. provisional patent application No. 62/730,286 filed on Sep. 12, 2018, the contents of which are incorporated herein by reference in their entirety.

FIELD

The present application relates to the treatment of nematode infections. For example, the application relates to the use of compounds of Formula I, and/or Formula II as defined herein for treatment of a nematode infection or a disease, disorder or condition arising from a nematode infection.

INTRODUCTION

The burden of parasitic nematodes on humanity is severe. The WHO estimates that over two billion people are infected with at least one parasitic nematode species. Chronic infection can cause dietary deficiency, anemia, developmental delay, elephantiasis, blindness, and death. Human infection in the west is increasing, coincident with a warming climate and the movement of sub-tropical species northward. Intestinal nematode infections alone are responsible for an estimated disease burden of 3.4 million disability-adjusted life-years. Furthermore, nematode infestation of food increases costs and contributes to malnutrition. Nematodes have evolved widespread resistance to nearly every anthelmintic (anti-worm) drug on the market. Hence, there is a dire need for the development of new compounds that kill parasitic worms.

Most anthelmintics disrupt the worm's nervous system, which ultimately allows the mammalian host to clear the infection. For example, key targets of ivermectin are glutamate-gated chloride channels of the nervous system. Ivermectin agonizes these channels and hyperpolarizes the cell, in turn leading to paralysis. Similarly, levamisole agonizes nicotinic acetylcholine receptors leading to depolarization of muscles and, in turn, paralysis.

SUMMARY

It has been shown herein that compounds of Formula I and/or II provide inhibitory activity against species of nematodes such as *Cooperia oncophora, Haemonchus contortus*, and *Caenorhabditis elegans*.

Accordingly, in one embodiment, the present application includes methods and uses for treating or preventing a nematode infection comprising administering an effective amount of a compound of Formula I

I and/or a pharmaceutically acceptable salt and/or solvate thereof to a subject in need thereof wherein L is $C_{0-4}$alkylene;

$R^1$ is phenyl, $C_{3-8}$cycloalkyl or $C_{3-8}$cycloalkene, each of which is unsubstituted or substituted with one or two substituents independently selected from $C_{1-4}$alkyl, $C_{1-4}$fluoroalkyl and $C_{1-4}$alkyl substituted with Cl or CN; and $R^2$ is H, $NO_2$, Cl, F or CN.

In one embodiment, the present application includes methods and uses for treating or preventing a nematode infection comprising administering an effective amount of a compound of Formula II

II and/or a pharmaceutically acceptable salt and/or solvate thereof to a subject in need thereof.

In some embodiments, the present application includes methods and uses of treating or preventing a disease, disorder or condition arising from a nematode infection comprising administering an effective amount a compound of Formula I

I and/or a pharmaceutically acceptable salt and/or solvate thereof to a subject in need thereof wherein L is $C_{0-4}$alkylene;

$R^1$ is phenyl, $C_{3-8}$cycloalkyl or $C_{3-8}$cycloalkene, each of which is unsubstituted or substituted with one or two substituents independently selected from $C_{1-4}$alkyl, $C_{1-4}$fluoroalkyl and $C_{1-4}$alkyl substituted with Cl or CN; and

$R^2$ is H, $NO_2$, Cl, F or CN.

In some embodiments, the present application includes methods and uses of treating or preventing a disease, disorder or condition arising from a nematode infection comprising administering an effective amount of a compound of Formula II and/or a pharmaceutically acceptable salt and/or solvate thereof to a subject in need thereof.

In some embodiments, the present application includes pharmaceutical compositions comprising a pharmaceutically acceptable carrier and a compound of Formula and/or a pharmaceutically acceptable salt and/or solvate thereof wherein
L is $C_{0-4}$alkylene;
$R^1$ is phenyl, $C_{3-8}$cycloalkyl or $C_{3-8}$cycloalkene, each of which is unsubstituted or substituted with one or two substituents independently selected from $C_{1-4}$alkyl, $C_{1-4}$fluoroalkyl and $C_{1-4}$alkyl substituted with Cl or CN; and
$R^2$ is H, $NO_2$, Cl, F or CN; and
wherein the compound of Formula I is present in an amount effective to treat a nematode infection in a subject in need thereof.

In some embodiments, the present application includes pharmaceutical compositions comprising a pharmaceutically acceptable carrier and a compound of Formula and/or a pharmaceutically acceptable salt and/or solvate thereof, wherein the compound of Formula II is present in an amount effective to treat a nematode infection in a subject in need thereof.

In some embodiments, the present application includes uses of pharmaceutical compositions comprising a compound of Formula I and/or II for treating or preventing a nematode infection or a disease, a disorder, or a condition arising from a nematode infection in a subject in need thereof.

In some embodiments, the present application includes nematicidal compositions comprising a carrier and a compound of Formula I and/or a salt and/or solvate thereof
wherein
L is $C_{0-4}$alkylene;
$R^1$ is phenyl, $C_{3-8}$cycloalkyl or $C_{3-8}$cycloalkene, each of which is unsubstituted or substituted with one or two substituents independently selected from $C_{1-4}$alkyl, $C_{1-4}$fluoroalkyl and $C_{1-4}$alkyl substituted with Cl or CN; and
$R^2$ is H, $NO_2$, Cl, F or CN; and
wherein the compound of Formula I is present in an amount effective to treat a nematode infection in a subject in need thereof.

In some embodiments, the present application includes nematicidal compositions comprising a carrier and a compound of Formula II and/or a salt, and/or solvate thereof wherein the compound of Formula II is present in an amount effective to treat a nematode infection in a subject in need thereof.

In some embodiments, the present application includes uses of the nematicidal composition described herein for treating or preventing a nematode infection or a disease, a disorder, or a condition arising from a nematode infection in a subject in need thereof.

In some embodiments, the present application includes methods of treating or preventing a nematode infection comprising administering an effective amount of a nematicidal composition described herein to a subject in need thereof.

Other features and advantages of the present application will become apparent from the following detailed description. It should be understood, however, that the detailed description and the specific examples, while indicating embodiments of the application, are given by way of illustration only and the scope of the claims should not be limited by these embodiments, but should be given the broadest interpretation consistent with the description as a whole.

DRAWINGS

The embodiments of the application will now be described in greater detail with reference to the attached drawings in which.

DESCRIPTION OF VARIOUS EMBODIMENTS

I. Definitions

Unless otherwise indicated, the definitions and embodiments described in this and other sections are intended to be applicable to all embodiments and aspects of the present application herein described for which they are suitable as would be understood by a person skilled in the art.

In understanding the scope of the present application, the term "comprising" and its derivatives, as used herein, are intended to be open ended terms that specify the presence of the stated features, elements, components, groups, integers, and/or steps, but do not exclude the presence of other unstated features, elements, components, groups, integers and/or steps. The foregoing also applies to words having similar meanings such as the terms, "including", "having" and their derivatives.

The term "consisting" and its derivatives, as used herein, are intended to be closed terms that specify the presence of the stated features, elements, components, groups, integers, and/or steps, but exclude the presence of other unstated features, elements, components, groups, integers and/or steps.

The term "consisting essentially of", as used herein, is intended to specify the presence of the stated features, elements, components, groups, integers, and/or steps as well as those that do not materially affect the basic and novel characteristic(s) of features, elements, components, groups, integers, and/or steps.

Terms of degree such as "substantially", "about" and "approximately" as used herein mean a reasonable amount of deviation of the modified term such that the end result is not significantly changed. These terms of degree should be construed as including a deviation of at least ±5% of the modified term if this deviation would not negate the meaning of the word it modifies.

As used in this application, the singular forms "a", "an" and "the" include plural references unless the content clearly dictates otherwise. For example, an embodiment including "a compound" should be understood to present certain aspects with compound or two or more additional compounds.

In embodiments comprising an "additional" or "second" component, such as an additional or second compound, the second component as used herein is chemically different from the other components or first component. A "third" component is different from the other, first, and second components, and further enumerated or "additional" components are similarly different.

The term "and/or" as used herein means that the listed items are present, or used, individually or in combination. In effect, this term means that "at least one of" or "one or more" of the listed items is used or present. The term "and/or" with respect to pharmaceutically acceptable, salts and/or solvates thereof means that referenced compounds exist as individual salts or hydrates, as well as a combination of, for example, a salt of a solvate of a compound.

The term "nematode infection" as used herein refers to an invasion of cells or bodily tissues by a foreign undesirable nematode.

The term "anthelmintic" or "anthelmintics" as used herein refers to a group of antiparasitic drug used in the treatment and prevention of nematode infections.

As used herein, a compound with "anthelmintic activity" is a compound, which when tested, has measurable nematode-killing activity or results in sterility or reduced fertility in the nematodes such that fewer viable or no offspring result, or compromises the ability of the nematode to infect or reproduce in its host, or interferes with the growth or development of a nematode. The compound may also display nematode repellant properties.

The term "pharmaceutically acceptable salt" means an acid addition salt or a basic addition salt suitable for, or compatible with, the treatment of subjects.

The term "pharmaceutically acceptable salts" embraces salts commonly used to form addition salts of free acids or free bases. The nature of the salt is not critical, provided that it is pharmaceutically-acceptable. Suitable pharmaceutically acceptable acid addition salts are prepared from an inorganic acid or an organic acid. Examples of such inorganic acids include, without limitation, hydrochloric, hydrobromic, hydroiodic, nitric, carbonic, sulfuric and phosphoric acid. Examples of appropriate organic acids include, for example, aliphatic, cycloaliphatic, aromatic, arylaliphatic, heterocyclic, carboxylic and sulfonic classes of organic acids, examples of which include, without limitation, formic, acetic, propionic, succinic, glycolic, gluconic, maleic, embonic (pamoic), methanesulfonic, ethanesulfonic, 2-hydroxyethanesulfonic, pantothenic, benzenesulfonic, toluenesulfonic, sulfanilic, mesylic, cyclohexylaminosulfonic, stearic, algenic, β-hydroxybutyric, malonic, galactic, and galacturonic acid. Suitable pharmaceutically-acceptable base addition salts include, but are not limited to, metallic salts made from aluminum, calcium, lithium, magnesium, potassium, sodium and zinc or organic salts made from N,N'-dibenzylethylenediamine, chloroprocaine, choline, diethanolamine, ethylenediamine, N-methylglucamine, lysine and procaine.

The term "solvates" as used herein refers to complexes formed between a compound and a solvent from which the compound is precipitated or in which the compound is made. Accordingly, the term "solvate" as used herein means a compound, or a salt a compound, wherein molecules of a suitable solvent are incorporated in the crystal lattice. Examples of suitable solvents are ethanol, water and the like. When water is the solvent, the molecule is referred to as a "hydrate".

The term "pharmaceutically acceptable solvate" means a solvate suitable for, or compatible with, the treatment of subjects. For pharmaceutically acceptable solvates, a suitable solvent is physiologically tolerable at the dosage used or administered.

The term "compound(s) of the application" as used herein refers to a compound of Formula I or Formula II and/or a pharmaceutically acceptable salt, and/or solvate thereof.

The term "wact-45" or "w-45" as used herein refers to the compound of Formula Ia. The term "compounds of wact-45 family" or "compounds of w-45 family" refers to compounds of Formula I.

The term "wact-45b" or "w-45b" as used herein refers to the compound of Formula Ib. The term "wact-46" or "w-46" as used herein refers to the compound of Formula Id. The term "wact-47" or "w-47" as used herein refers to the compound of Formula Ie. The term "wact-6" or "w-6" as used herein refers to the compound of Formula Ic. The term "wact-45-RRE" or "w-45-RRE" as used herein refers to the compound of Formula If.

The term "wact-379" or "w-379" as used herein refers to the compound of Formula II.

The expression "disease, disorder or condition arising from a nematode infection" as used herein refers to any disease, disorder or condition that is directly or indirectly caused by the presence of a nematode infection in a subject.

The term "subject" as used herein includes plants, seeds, soil, and all members of the animal kingdom including mammals and birds, and their food. Thus, the methods of the present application are applicable to plant treatment, human therapy and veterinary applications.

When used, for example, with respect to the methods of treatment, uses, compositions and kits of the application, a subject, for example a subject "in need thereof" is a subject who has been diagnosed with, is suspected of having, may come in to contact with, and/or was previously treated for a nematode infection or a disease, disorder or condition arising from a nematode infection.

When used, for example, in respect to plant treatments, the compounds and/or compositions may be delivered by several means including pre-planting, post-planting and as a feed additive, drench, external application, pill or by injection.

The term "pharmaceutical composition" as used herein refers to a composition of matter for pharmaceutical use.

The term "pharmaceutically acceptable" means compatible with the treatment of subjects.

The term "nematicidal composition" as used here in refers to a composition of matter for managing one or more nematode infections.

The term "administered" as used herein means administration of an effective amount of a compound, including compounds of Formula I or II, or a salt and/or solvate thereof, to a cell either in cell culture or in a subject.

As used herein, the term "effective amount" or "therapeutically effective amount" means an amount effective, at dosages and for periods of time necessary to achieve a desired result. For example, in the context of treating a nematode infection, or a disease, disorder or condition arising from a nematode infection, an effective amount of a compound is an amount that, for example, reduces the nematode infection compared to the nematode infection without administration of the compound. By "reducing the infection", it is meant, for example, reducing the amount of the infectious agent in the subject and/or reducing the symptoms of the infection. The amount of a given compound or composition that will correspond to such an amount will vary depending upon various factors, such as the given compound or composition, the formulation, the route of administration, the type of condition, disease or disorder, the identity of the subject being treated, and the like, but can nevertheless be routinely determined by one skilled in the art.

The terms "to treat", "treating" and "treatment" as used herein and as is well understood in the art, means an approach for obtaining beneficial or desired results, including clinical results. Beneficial or desired clinical results include, but are not limited to, diminishment of extent of nematode infection, stabilization (i.e. not worsening) of the state of the nematode infection, preventing spread of the nematode infection, delay or slowing of infection progression, amelioration or palliation of the nematode infectious state, diminishment of the reoccurrence of nematode infection, diminishment, stabilization, alleviation or amelioration of one or more diseases, disorders or conditions arising from the nematode infection, diminishment of the reoccurrence of one or more diseases, disorders or conditions arising from the nematode infection, and remission of the nematode infection and/or one or more symptoms or conditions arising from the nematode infection, whether partial or total, whether detectable or undetectable. "To treat", "treating" and "treatment" can also mean prolonging survival as compared to expected survival if not receiving treatment. "To treat", "treating" and "treatment" as used herein also include prophylactic treatment. For example, a subject with an early nematode infection is treated to prevent progression, or alternatively a subject in remission is treated to prevent recurrence.

"Palliating" an infection, disease, disorder and/or condition means that the extent and/or undesirable manifestations of an infection, disease, disorder and/or condition are lessened and/or time course of the progression is slowed or lengthened, as compared to not treating the infection, disease, disorder and/or condition.

The term "prevention" or "prophylaxis" and the like as used herein refers to a reduction in the risk or probability of a subject becoming afflicted with a nematode infection and/or a disease, disorder and/or condition arising from a nematode infection or manifesting a symptom associated with a nematode infection and/or a disease, disorder and/or condition arising from a nematode infection.

II. Methods and Uses of the Application

Families of small molecule compounds have been identified that incapacitate parasitic nematodes, and advantageously show no genetic resistance. This suggest that resistance to these compounds will be less likely to develop in the wild.

The present application includes methods and uses for treating or preventing a nematode infection comprising administering an effective amount of a compound of Formula I and/or a pharmaceutically acceptable salt and/or solvate thereof to a subject in need thereof wherein L is $C_{0-4}$alkylene;

$R^1$ is phenyl, $C_{3-8}$cycloalkyl or $C_{3-8}$cycloalkene, each of which is unsubstituted or substituted with one or two substituents independently selected from $C_{1-4}$alkyl, $C_{1-4}$fluoroalkyl and $C_{1-4}$alkyl substituted with Cl or CN; and $R^2$ is H, $NO_2$, Cl, F or CN.

In one embodiment, the present application includes methods and uses for treating or preventing a nematode infection comprising administering an effective amount of a compound of Formula II

II and/or a pharmaceutically acceptable salt and/or solvate thereof to a subject in need thereof.

In some embodiments, the present application includes methods and uses of treating or preventing a disease, disorder or condition arising from a nematode infection comprising administering an effective amount a compound of Formula I

I and/or a pharmaceutically acceptable salt and/or solvate thereof to a subject in need thereof wherein L is $C_{0-4}$alkylene;

$R^1$ is phenyl, $C_{3-8}$cycloalkyl or $C_{3-8}$cycloalkene, each of which is unsubstituted or substituted with one or two substituents independently selected from $C_{1-4}$alkyl, $C_{1-4}$fluoroalkyl and $C_{1-4}$alkyl substituted with Cl or CN; and $R^2$ is H, $NO_2$, Cl, F or CN.

In some embodiments, the present application includes methods and uses of treating or preventing a disease, disorder or condition arising from a nematode infection comprising administering an effective amount of a compound of Formula II

II and/or a pharmaceutically acceptable salt and/or solvate thereof to a subject in need thereof.

In some embodiments, the present application includes uses of pharmaceutical compositions comprising a compound of Formula I and/or II for treating or preventing a nematode infection or a disease, a disorder, or a condition arising from a nematode infection in a subject in need thereof.

In some embodiments, the present application includes methods of treating or preventing a nematode infection comprising administering an effective amount of a nematicidal composition comprising a compound of Formula I and/or II described herein to a subject in need thereof.

In some embodiments, the present application includes uses of a nematicidal composition comprising a compound of Formula I and/or II described herein for treating or preventing a nematode infection or a disease, a disorder, or a confition arising from a nematode infection in a subject in need thereof.

In some embodiments, the L of compound of Formula I is $CH_2$.

In some embodiments, the L of compound of Formula I is absent, such that $R^1$ is directly bonded to the N atom.

In some embodiments, the compound of Formula I is selected from

Ia

Ib

Ic

In some embodiments, the nematode infection is an infection of a nematode of a species selected from *Cooperia oncophora*, *Haemonchus contortus*, and *Caenorhabditis elegans*.

Treatment methods comprise administering to a subject one or more compounds of the application, and optionally consists of a single administration, or alternatively comprises a series of administrations. The length of the treatment period depends on a variety of factors, such as the severity of the infection, disease, disorder or condition, the age of the subject, the dosage of the one or more compounds of the application, the activity of one or more compounds of the application, or a combination thereof.

In an embodiment, the one or more compounds of the application are administered or used as soon as possible after exposure to the nematode. In an embodiment, the one or more compounds of the application are administered or used until treatment of the nematode infection, disease disorder or condition is achieved. For example, until complete elimination of the nematode is achieved, or until the number of nematode has been reduced to the point where the subject's defenses are no longer overwhelmed and can kill any remaining nematode.

In an embodiment, the methods of the present application comprise administering an effective amount of a compound or a composition of the application to a subject selected from humans, mammals, birds, vertebrates, plants, seeds, and soil.

In an embodiment, the uses of the present application of a compound or a composition of the application are in a subject selected from humans, mammals, birds, vertebrates, plants, seeds, and soil.

In some embodiments, the nematode infects plants and the nematicidal composition is administered to the soil or to plants. In some embodiments, the nematicidal composition is administered to soil before planting. In some embodiments, the nematicidal composition is administered to soil after planting. In some embodiments, the nematicidal composition is administered to soil using a drip system. In some embodiments, the nematicidal composition is administered to soil using a drench system. In some embodiments, the nematicidal composition is administered to plant roots or plant foliage (e.g., leaves, stems). In some embodiments the nematicide composition is tilled into the soil or administered in furrow. In some embodiments, the nematicidal composition is administered to seeds.

In some embodiments, the nematode parasite infects a vertebrate. In some embodiments, the nematicidal composition is administered to non-human vertebrate. In some embodiments, the nematicidal composition is administered to a human. In some embodiments, the nematicidal composition is formulated as a drench to be administered to a non-human animal. In some embodiments, the nematicidal composition is formulated as an orally administered drug. In some embodiments, the nematicidal composition is formulated as an injectable drug. In some embodiments, the nematicidal composition is formulated for topical applications such as pour-ons, or for the use in tags or collars.

In some embodiments, the methods of the application comprise administering a compound or a composition of the application through one or more means selected from pre-planting, post-planting, as a feed additive, a drench, an external application, a pill and by injection.

In some embodiments, the present application includes methods of reducing the viability or fecundity or slowing the growth or development or inhibiting the infectivity of a nematode using a compound or a composition of the application as described herein.

In some embodiments, the present application includes methods of reducing the viability or fecundity or slowing the growth or development or inhibiting the infectivity of a nematode using a compound or a composition of the application as described herein, the methods comprising administering a compound or a composition of the application to subject selected from a human, a mammal, a bird, a vertebrate in general, a plant, a seed, or soil. In some examples, the bird can be a domesticated fowl; the mammal can be a domesticated animal and/or livestock.

The dosage of the one or more compounds of the application, varies depending on many factors such as the pharmacodynamic properties thereof, the mode of administration, the age, health and weight/mass of the subject, the nature and extent of the symptoms, the frequency of the treatment and the type of concurrent treatment, if any, and the clearance rate in the subject to be treated. One of skill in the art can determine the appropriate dosage based on the above factors. The one or more compounds of the application may be administered initially in a suitable dosage that may be adjusted as required, depending on the response.

Compounds can be tested for anthelmintic activity using methods known in the art. For example, the compound is combined with nematodes, e.g., in a well of microtiter dish, in liquid or solid media or in the soil containing the agent. Staged nematodes are placed on the media. The time of survival, viability of offspring, and/or the movement of the nematodes are measured. An agent with "anthelmintic or anthelminthic or antihelmthic activity" can, for example, reduce the survival time of adult nematodes relative to unexposed similarly staged adults, e.g., by about 20%, 40%, 60%, 80%, or more. In the alternative, an agent with "anthelmintic or anthelminthic or antihelminthic activity" may also cause the nematodes to cease replicating, regenerating, and/or producing viable progeny, e.g., by about 20%, 40%, 60%, 80%, or more. The effect may be apparent immediately or in successive generations.

III. Compositions of the Application

In some embodiments, the present application includes pharmaceutical compositions comprising a pharmaceutically acceptable carrier and a compound of Formula and/or a pharmaceutically acceptable salt and/or solvate thereof to a subject in need thereof wherein:

L is $C_{0-4}$alkylene;

$R^1$ is phenyl, $C_{3-8}$cycloalkyl or $C_{3-8}$cycloalkene, each of which is unsubstituted or substituted with one or two substituents independently selected from $C_{1-4}$alkyl, $C_{1-4}$fluoroalkyl and $C_{1-4}$alkyl substituted with Cl or CN; and $R^2$ is H, $NO_2$, Cl, F or CN; and wherein the compound of Formula I is present in an amount effective to treat a nematode infection in a subject in need thereof.

In some embodiments, the present application includes pharmaceutical compositions comprising a pharmaceutically acceptable carrier and a compound of Formula II and/or a pharmaceutically acceptable salt and/or solvate thereof, wherein the compound of Formula II is present in an amount effective to treat a nematode infection in a subject in need thereof.

In some embodiments, the present application includes uses of pharmaceutical compositions comprising a compound of Formula I or II for treating or preventing a nematode infection or a disease, a disorder, or a condition arising from a nematode infection in a subject in need thereof.

In some embodiments, the present application includes a nematicidal composition comprising a carrier and a compound of Formula I and/or a salt and/or solvate thereof wherein:

L is $C_{0-4}$alkylene;

$R^1$ is phenyl, $C_{3-8}$cycloalkyl or $C_{3-8}$cycloalkene, each of which is unsubstituted or substituted with one or two substituents independently selected from $C_{1-4}$alkyl, $C_{1-4}$fluoroalkyl and $C_{1-4}$alkyl substituted with Cl or CN; and $R^2$ is H, $NO_2$, Cl, F or CN; and wherein the compound of Formula I is present in an amount effective to treat a nematode infection in a subject in need thereof.

In some embodiments, the present application includes a nematicidal composition comprising a carrier and a compound of Formula II and/or a salt and/or solvate thereof wherein the compound of Formula II is present in an amount effective to treat a nematode infection in a subject in need thereof.

In some embodiments, the linker L of compound of Formula I is $CH_2$.

In some embodiments, the linker L of compound of Formula I is optional and absent, such that $R^1$ is directly bonded to the N atom.

In some embodiments, the compound of Formula I is selected from

-continued

In some embodiments, the nematode infection is an infection of a nematode of the following non-limiting, exemplary genera: *Caenorhabditis, Nippostrongyles, Anguina, Ditylenchus, Tylenchorhynchus, Pratylenchus, Radopholus, Hirschmanniella, Nacobbus, Hoplolaimus, Scutellonema, Rotylenchus, Helicotylenchus, Rotylenchulus, Belonolaimus, Heterodera,* other cyst nematodes, *Meloidogyne, Criconemoides, Hemicycliophora, Paratylenchus, Tylenchulus, Aphelenchoides, Bursaphelenchus, Rhadinaphelenchus, Longidorus, Xiphinema, Trichodorus, Paratrichodorus, Dirofiliaria, Onchocerca, Brugia, Acanthocheilonema, Aelurostrongylus, Anchlostoma, Angiostrongylus, Ascaris, Bunostomum, Capillaria, Chabertia, Cooperia, Crenosoma, Dictyocaulus, Dioctophyme, Dipetalonema, Dracunculus, Enterobius, Filaroides, Haemonchus, Lagochilascaris, Loa, Manseonella, Muellerius, Necator, Nematodirus, Oesophagostomum, Ostertagia, Parafilaria, Parascaris, Physaloptera, Protostrongylus, Setaria, Spirocerca, Stephanogilaria, Strongy hides, Strongylus, Thelazia, Toxascaris, Toxocara, Trichinella, Trichostrongylus, Trichuris, Uncinaria* or *Wuchereria.* In some embodiments, the nematodes are of the genera *Cooperia, Haemonchus, Caenorhabditis, Nippostrongyles, Dirofilaria, Onchocerca, Brugia, Acanthocheilonema, Dipetalonema, Loa, Mansonella, Parafilaria, Setaria, Stephanofilaria, Wucheria, Pratylenchus, Heterodera, Meloidogyne* or *Paratylenchus.* In some embodiments the nemotodes are of the species *Cooperia oncophora, Haemonchus contortus, Caenorhabditis elegans, Nippostrongyles brasiliensis, Ancylostoma caninum, Haemonchus contortus, Trichinella spiralis, Trichurs muris, Dirofilaria immitis, Dirofilaria tenuis, Dirofilaria repens, Dirofilari ursi, Ascaris suum, Toxocara canis, Toxocara cati, Strongyloides ratti, Parastrongyloides trichosuri, Heterodera glycines, Globodera pallida, Meloidogyne javanica, Meloidogyne incognita, Meloidogyne arenaria, Radopholus similis, Longidorus elongatus, Meloidogyne hapla* or *Pratylenchus penetrans.*

In some embodiments, the nematode infection is an infection of a nematode of a species selected from *Cooperia oncophora, Haemonchus contortus, Dirofilaria, Nippostrongyles brasiliensis* and *Caenorhabditis elegans.*

In some embodiments, the subject is selected from humans, mammals, birds, vertebrates, plants, seeds, and soil.

In some embodiments, the nematicidal compositions further comprise one or more agricultural excipients.

In some embodiments, the nematicidal compositions further comprise one or more agriculturally acceptable excipients.

For example, in some embodiments, the nematicidal compositions further comprises an aqueous surfactant. Examples of surfactants that can be used include, Span 20, Span 40, Span 80, Span 85, Tween 20, Tween 40, Tween 80, Tween 85, Triton X 100, Makon 10, Igepal CO 630, Brij 35, Brij 97, Tergitol TMN 6, Dowfax 3B2, Physan and Toximul TA 15, and mixtures therof.

In some embodiments, the nematicidal composition further comprises a permeation enhancer (e.g., cyclodextrin). In some embodiments, the nematicidal composition further comprises a co-solvent. Examples of co-solvents that can be used include ethyl lactate, methyl soyate/ethyl lactate co-solvent blends (e.g., Steposol), isopropanol, acetone, 1,2-propanediol, n-alkylpyrrolidones (e.g., the Agsolex series), a petroleum based-oil (e.g., aromatic 200) or a mineral oil (e.g., paraffin oil), or mixtures thereof. In some embodiments, the nematicidal composition further comprises another pesticide (e.g., nematicide, insecticide or fungicide) such as an avermectin (e.g., ivermectin), milbemycin, imidacloprid, aldicarb, oxamyl, fenamiphos, fosthiazate, metam sodium, etridiazole, penta-chloro-nitrobenzene (PCNB), flutolanil, metalaxyl, mefonoxam, and fosetyl-al, or mixtures thereof. Useful fungicides include, but are not limited to, silthiofam, fludioxonil, myclobutanil, azoxystrobin, chlorothalonil, propiconazole, tebuconazole and pyraclostrobin, or mixtures thereof. In some embodiments, the nematicidal composition may also comprise herbicides (e.g., trifloxysulfuron, glyphosate, halosulfuron) and other chemicals for disease control (e.g., chitosan).

In some embodiments, the application also includes a nematicidal feed for a non-human vertebrate including:
(a) a feed; and (b) a nematicidal composition, of the application.

In some embodiments, the feed is selected from: soy, wheat, corn, sorghum, millet, alfalfa, clover, and rye, and mixtures thereof. Also described are feeds that have been supplemented to include one or more of the compounds of the application. A nematicidal feed for a non-human vertebrate can comprise: (a) an animal feed; and (b) an effective amount of a nematicidal compound of the application.

In some embodiments, the pharmaceutical compositions further comprise one or more pharmaceutically acceptable excipients. Conventional procedures and ingredients for the selection and preparation of suitable pharmaceutical compositions are described, for example, in Remington's Pharmaceutical Sciences (2000-20th edition) and in The United States Pharmacopeia: The National Formulary (USP 24 NF19) published in 1999.

For example, the pharmaceutical forms suitable for injectable use include sterile aqueous solutions or dispersions and sterile powders for the extemporaneous preparation of sterile injectable solutions or dispersions. In all cases, the form is sterile and fluid to the extent that easy syringability exists.

In an embodiment, parenteral administration is by continuous infusion over a selected period of time. Solutions suitable for parenteral administration are prepared by known methods by a person skilled in the art. For example, the compounds of the application are prepared in water optionally mixed with a surfactant such as hydroxypropylcellulose. Dispersions are also prepared in glycerol, liquid polyethylene glycols, DMSO and mixtures thereof with or without alcohol, and in oils. Under ordinary conditions of storage and use, these preparations contain a preservative to prevent the growth of microorganisms.

Compositions for nasal administration are conveniently formulated as aerosols, drops, gels or powders. Aerosol formulations typically comprise a solution or fine suspension of the active substance in a physiologically acceptable aqueous or non-aqueous solvent and are usually presented in single or multidose quantities in sterile form in a sealed container, which take the form of a cartridge or refill for use with an atomising device. Alternatively, the sealed container is a unitary dispensing device such as a single dose nasal inhaler or an aerosol dispenser fitted with a metering valve, which is intended for disposal after use. Where the dosage form comprises an aerosol dispenser, it contains a propellant, which is, for example, a compressed gas such as compressed air or an organic propellant such as fluorochlorohydrocarbon. In an embodiment, the aerosol dosage forms take the form of a pump-atomizer.

Compositions suitable for buccal or sublingual administration include tablets, lozenges, and pastilles, wherein the active ingredient is formulated with a carrier such as sugar, acacia, tragacanth, gelatin and/or glycerine. Compositions for rectal administration are conveniently in the form of suppositories containing a conventional suppository base such as cocoa butter.

In another embodiment, compounds of the application are orally administered, for example, with an inert diluent or with an assimilable edible carrier, or they are enclosed in hard or soft shell gelatin capsules, or they are compressed into tablets, or they are incorporated directly with the food of a diet. For oral administration, the compounds of the application may be incorporated with excipients and used in the form of, for example, ingestible tablets, buccal tablets, troches, capsules, elixirs, suspensions, syrups, wafers, and the like. Oral dosage forms also include modified release, for example immediate release and timed-release, formulations. Examples of modified-release formulations include, for example, sustained-release (SR), extended-release (ER, XR, or XL), time-release or timed-release, controlled-release (CR), or continuous-release (CR or Contin), employed, for example, in the form of a coated tablet, an osmotic delivery device, a coated capsule, a microencapsulated microsphere, an agglomerated particle, e.g., molecular sieving type particles, or, a fine hollow permeable fiber bundle, or chopped hollow permeable fibers, agglomerated or held in a fibrous packet. In an embodiment, timed-release compositions are, formulated, as liposomes or those wherein the active compound is protected with differentially degradable coatings, such as by microencapsulation, multiple coatings, etc. Liposome delivery systems include, for example, small unilamellar vesicles, large unilamellar vesicles and multilamellar vesicles. In an embodiment, liposomes are formed from a variety of lipids, such as cholesterol, stearylamine or phosphatidylcholines.

It is also possible to freeze-dry the compounds of the application and use the lyophilizate obtained, for example, for the preparation of products for injection.

The compounds of the application are either commercially available or may be prepared using methods known in the art.

The formation of a desired compound salt is achieved using standard techniques. For example, the neutral compound is treated with an acid or base in a suitable solvent and the formed salt is isolated by filtration, extraction or any other suitable method.

The formation of solvates will vary depending on the compound and the solvate. In general, solvates are formed by dissolving the compound in the appropriate solvent and isolating the solvate by cooling or using an antisolvent. The solvate is typically dried or azeotroped under ambient conditions. The selection of suitable conditions to form a particular solvate can be made by a person skilled in the art.

The following non-limiting examples are illustrative of the present application. As is apparent to those skilled in the art, many of the details of the examples may be changed while still practicing the methods, compositions and kits described herein.

IV. EXAMPLES

Example 1 Screening of Compounds

Because of their dependence on a host, parasitic nematodes are difficult to culture, maintain and sustain. Therefore, to screen for antithelmintic compounds, the non-parasitic nematode, *C. elegans*, was used as a model system, then compound leads were investigated in parasitic nematodes.

Molecules that can modulate the egg-laying rate of the *C. elegans* (which can be done in medium-throughput fashion) were identified first and then the hits' ability to disrupt worm locomotion was examined using lower-throughput techniques. Egg-laying is a convenient system with which to interrogate neuromuscular control because it's digital output (an egg is either laid or not) can be easily quantified. Wild type hermaphrodites carry 10-15 eggs in their uterus and lay ~one egg per hour in the liquid (control) buffer used for liquid worm culture. Egg-laying is principally regulated by cholinergic and serotonergic signaling via conserved receptors.

To identify egg-laying (Egl) modulators, a medium-throughput line-scanning microscope capable of imaging a 96 well plate in just over 2 minutes was used. From the resulting images, image analysis software to count the number of eggs laid per adult per hour in each well was used. Small molecules at a final concentration of 60 µM were screened, which is a technically convenient concentration where most molecules stay in solution. This may be considered a high concentration for most screening platforms, but is suitable for *C. elegans* because of the nematode's robust xenobiotic defenses.

A collection of 486 synthetic small molecules that have previously shown some effect on worm growth was screened. These molecules are from Chembridge Inc., are drug-like in their physico-chemical properties, and have relatively uncharacterized bioactivity. To identify Egl-stimulators, small molecules were screened in a benign control buffer. To identify Egl-inhibitors, molecules were screened in the background of 2.5 mM serotonin plus 7.7 mM nicotine, which is a cocktail that was empirically determined to induce robust egg-laying in liquid media. Molecules that reproducibly ($p<0.05$) modulate egg-laying two fold greater than control conditions were considered 'stimulators', and molecules that modulate egg-laying two fold less than stimulating conditions were considered 'inhibitors'.

In the above-described assay, 31 stimulators and 33 inhibitors of egg-laying were identified. A structural comparison of these hits using a Tanimoto™/FP2 similarity cutoff of 0.55 or greater revealed that many of the Egl-modulators belong to structurally-similar families. A network was generated using a Tanimoto™ chemical similarity cut-off of 55%. Molecules that share structural similarity typically modulate egg laying similarly, suggesting a shared mechanism of action.

The ability of the 64 Egl hits to modulate the normal sinusoidal locomotion of wild type *C. elegans* was then examined. The animal's behaviour over the course of several hours was manually monitored while the animal moved atop a solid agar substrate containing the small molecule. Many different genes govern the sinusoidal locomotion of wild type *C. elegans*, but their mutation can lead to qualitatively distinct locomotory phenotypes. Hence, a distinct locomotory response to a small molecule can be suggestive of its mechanism of action.

Figure 1:
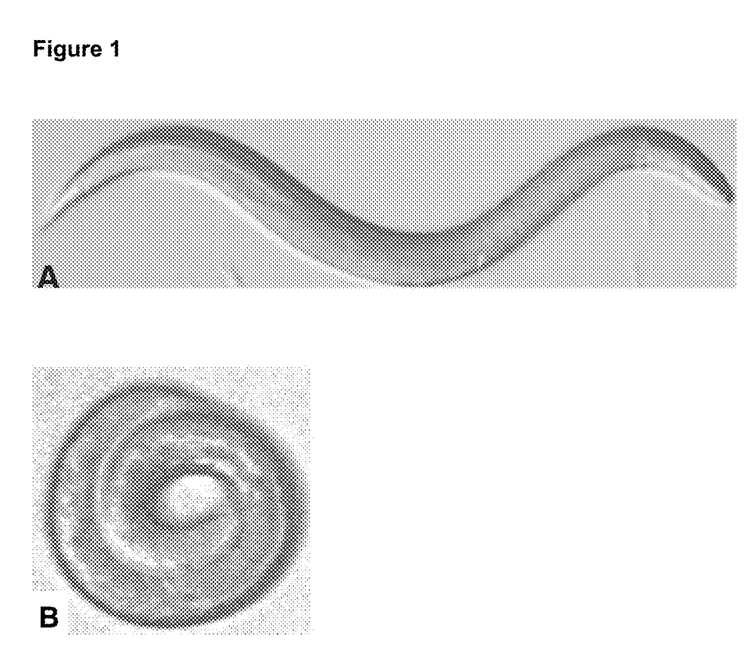
FIG. 1 shows movement defects induced by exemplary compounds including compound Ia. Panel A shows a negative control healthy *C. elegans* worm without drug. Panel B shows the "coiler defect" phenotype of a *C. elegans* worm in presence of exemplary Compound Ia.

Compared to the normal phenotype of the worm as shown in FIG. 1 panel A, 8 molecules that induce simultaneous anterior and posterior contraction (called a 'rubber-band' phenotype) were identified; 3 molecules that cause animals to turn along their circumferential axis (ca a 'shaker' phenotype) were identified; 3 molecules that cause the animal to coil like a snake (called a 'coiler' phenotype) were identified; 2 molecules that induce jerky uncoordination (called jerky-unc) were identified; 3 molecules that disrupt reverse locomotion were identified; and 3 that induce paralysis were identified.

Wact-45 (Compound Ia) induced a strong coiler phenotype (FIG. 1 panel B). Previous phylogenetic bioactivity analysis suggests that the activity of wact-45 (Compound Ia) might be restricted to nematodes. The coiler phenotype that is induced by compound Ia is consistent with a decrease in acetylcholine (ACh) levels at the synaptic cleft.

Example 2 Cytotoxicity of Exemplary Compound Ia

Figure 2:
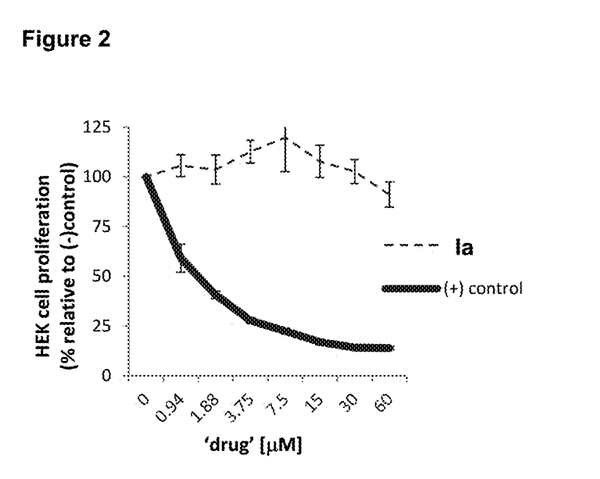
FIG. 2 shows impact of exemplary compound Ia (wact-45) on HEK293 cell proliferation compared to a positive control where dashed line shows data for exemplary compound Ia.

The cytotoxicity of exemplary compound Ia was investigated by measuring HEK293 cell proliferation in a dose-response analysis and no effect was found on HEK293 cell proliferation by exemplary compound Ia as shown in FIG. 2. A cytotoxic formulation was used as positive control. Experiments were performed in triplicates on different days. Cell viability was assess using a standard Celltiter Blue™ Cell Viability Assay (Promega). Compounds were added to cells in 96-well plates at time zero and cell viability assessed in 48 hours. Error bars indicate standard deviation.

Example 3 Compounds of Formula I Induce Coiler Phenotype

Three structurally-related molecules (Compound Ia, compound Ie and compounds Ic) induce a 'severe' snake-like coiler phenotype and paralysis (FIG. 1, panel B). Compound Id is a forth structurally-related molecule that induces a 'jerky-unc' phenotype. A detailed phenotypic analyses suggests that the animals exposed to these molecules phenotypically transit over time from jerky-unc to being coiled to being paralyzed, with exemplary compound Ia being the prototypical example.

Forward genetic screens were performed for mutants that can resist the early larval lethal effects of wact-6 (compound Ic) and wact-46 (compound Id). Over 200,000 F1 animals and over 100,000 F2 animals from randomly mutagenized parents/grandparents were screened. No mutants that could resist the lethal effects of wact-6 (compound Ic) and wact-46 (compound Id). This suggests that viable resistance may be difficult to achieve against this class of nematicide in the wild.

Example 4 Mechanism of Action: Compounds of Formula I Likely Inhibits Vesicular Acetylcholine Transporter (VAChT)

Two observations raised the possibility that the wact-45 family (compounds of Formula I) reduces acetylcholine (ACh) signalling. First, many mutant genes that yield a strong coiler phenotype are associated with disrupted cholinergic motorneuron development and/or with disrupted ACh production, release or reception. Second, the wact-45 family (compounds of Formula I) has structural similarity to vesamicol, which is a research tool that inhibits the vertebrate vesicular acetylcholine transporter (VAChT) (Table 1). VAChT transports cytoplasmic ACh into synaptic vesicles in the presynaptic membrane of all animals. Vesamicol is not useful as a medicine because it disrupts ACh signalling and is therefore toxic to vertebrates. In *C. elegans*, VAChT is encoded by unc-17, whose reduction-of-function phenotype is 'severe' coiling. It was therefore hypothesized that exemplary compound Ia inhibits UNC-17.

Exemplary compound Ia's inhibitory activity on UNC-17 was tested in several ways. First, the phenotype of exemplary compound Ia was compared to that of vesamicol. Vesamicol induces jerky-unc and coiling, but only at concentrations close to its limit of solubility on solid substrate. This analysis reveals that exemplary compound Ia is more than 30 times more potent than vesamicol for inducing locomotory defects in worms.

Figure 3:
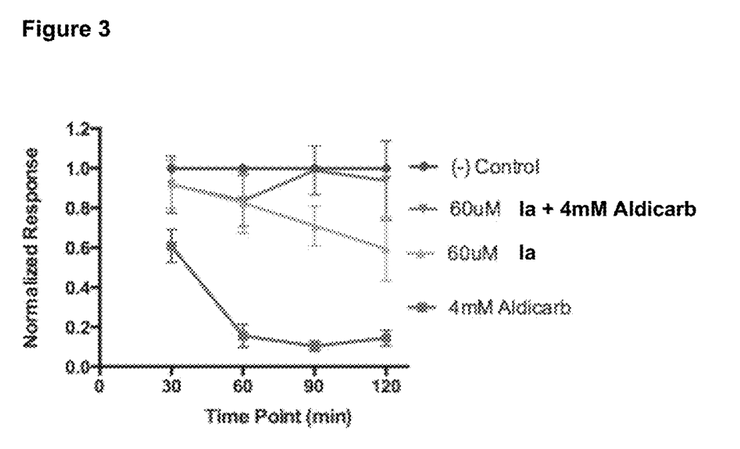
FIG. 3 shows drug-induced paralysis suppression in *C. elegans* in the presence of exemplary compound Ia (wact-45). Circle (•) indicates negative control where no drug is used. Square (■) shows positive control with Aldicarb, a paralysis-inducing drug. Downward-facing triangle (▼) indicates exemplary compound Ia used in combination with Aldicarb. Upward-facing triangle (▲) indicates exemplary compound Ia used alone.

Whether exemplary compound Ia can suppress the paralysis that is induced by aldicarb was tested. Aldicarb inhibits acetylcholinesterase, which normally catabolizes ACh at the synaptic cleft. Exemplary compound Ia's $EC_{50}$ for suppression of Aldicarb activity is 4.806 µM. Aldicarb treatment therefore results in excess ACh and paralyzes the animal due to excess muscle contraction. If exemplary compound Ia inhibits UNC-17 and results in lower levels of ACh at the synaptic cleft, then exemplary compound Ia should reduce aldicarb-induced paralysis. Indeed, an obvious reduction of aldicarb-induced paralysis by exemplary compound Ia was found ($p<0.001$) (FIG. 3).

Third, the interaction between exemplary compound Ia and various mutant strains of unc-17 was explored. If exemplary compound Ia inhibits UNC-17, then unc-17 reduction-of-function alleles should be hypersensitive to exemplary compound Ia. Indeed, the unc-17 hypomorphic alleles e245, e327, and e795 have heightened sensitivity to exemplary compound Ia ($p<0.001$). Previous work demonstrated that the C391Y mutation in human VAChT is essential for vesamicol binding. The orthologous mutation in UNC-17 is C370Y and exists in the unc-17 (md414) mutant, which also has weak reduction-of-function phenotypes. Without knowing that human VAChT (C391Y) fails to interact with vesamicol, the naïve expectation is that unc-17 (md414) would also be hypersensitive to wact-45. However, it was found that unc-17 (md414) is partially resistant to the effects of both wact-45 and vesamicol ($p=0.001$). Together, these chemical-genetic interactions indicate that wact-45 likely inhibits UNC-17 function.

Example 5 Bioactivity Profile of Exemplary Compound Ia

Compounds of the Formula I fully inhibit egg-hatching of the mammalian parasites *H. contortus* and *C. oncophora* at mid-micromolar concentrations (30-60 uM) and inhibit dog heartworm movement with an $ED_{50}$ in the low micromolar concentration range (2-10 uM) in ex-vivo assays. The compounds have little effect on HEK293 cell proliferation at any concentration tested as shown above in FIG. 2.

A dose-response analysis in fish of three compounds of Formula I showed that the molecules induce cardiac defects in the low micromolar range. However, exemplary compound Ia itself has the weakest cardiac defects of the three compounds, while compound Ie (which has relatively weak effects in worms), induced the strongest cardiac defects.

Example 6 Structural-Activity Relationship (SAR) of Compounds of Formula I and Bioactivity Profile A preliminary first round of SAR analyses using commercially available analogs of exemplary compound Ia was performed and the analogs' ability to induce locomotory defects in wild type fourth-stage *C. elegans* larvae (L4s) was tested. As expected, most analogs induced weaker locomotory phenotypes compared to compound Ia, the exception being wact-45b (compound Ib) (Table 1). Using this information, new analogs of exemplary compound Ia were synthesized, and the most potent analog to date, wact-45-RRE (compound If) (Table 1) was identified.

Table 1 shows the preliminary SAR study conducted on compounds of Formula I, where activity indicates the percent of animals that show coiled and/or paralysis after 60 min on solid substrate with a "drug" concentration 60 μM. If phenotype is observed, a dose-response analysis is performed. Exemplary compound Ia has an $EC_{50}$ of 12.8 μM.

TABLE 1

SAR of compounds of Formula I

| Compound | $R^2$ | L-$R^1$ | Activity (%) |
|---|---|---|---|
| Ia (wact-45) | $NO_2$ | cyclohexylmethyl | 90& +/− 5.4 |
| Ib (wact-45b) | $NO_2$ | 4-methylcyclohexylmethyl | 87% +/− 3.7 |
| Im (wact-45c) | $NO_2$ | benzyl | 0.00 |
| Ip (wact-45k) | $NO_2$ | 4-methylbenzyl | 0.00 |
| If (wact-45-RRE) | $NO_2$ | cyclopentylmethyl | 98% +/− 1.9 |
| Iq (wact-45-RRF) | CN | cyclopentylmethyl | 41% +/− 7.4 |
| Ir (wact-45-RRJ) | $NO_2$ | cyclopropylmethyl | 6% +/− 3.2 |
| Ic (wact-6) | $NO_2$ | 4-methylcyclohexylmethyl (CH3) | 71% +/− 2.1 |
| Id (wact-46) | $NO_2$ | norbornenylmethyl | 0.00 |
| Ie (wact-47) | $NO_2$ | cyclohex-3-enylmethyl | 19% +/− 8.0 |
| Vesamicol | — | — | 6% +/− 0.1 |
| Piperazine | — | — | 0.00 |

The invention claimed is:

1. A method of treating or preventing a nematode infection comprising administering an effective amount of a compound of Formula I and/or a pharmaceutically acceptable salt and/or solvate thereof to a subject in need thereof
wherein:
L is $C_{0-4}$alkylene;
$R^1$ is $C_{4-8}$cycloalkyl or $C_{4-8}$cycloalkene, each of which is unsubstituted or substituted with one or two substituents independently selected from $C_{1-4}$alkyl, $C_{1-4}$fluoroalkyl and $C_{1-4}$alkyl substituted with Cl or CN; and
$R^2$ is H, $NO_2$, Cl, F or CN.

2. The method of claim 1, wherein L is $CH_2$.

3. The method of claim 1, wherein the compound of Formula I is selected from

-continued

4. The method of claim 1, wherein the infection is an infection of a nematode of a species selected from *Cooperia oncophora, Haemonchus contortus*, and *Caenorhabditis elegans*.

5. The method claim 1, wherein the subject is selected from a human, a mammal, a bird, a plant, a seed, and soil.

6. A method of treating or preventing a disease, disorder or condition arising from a nematode infection comprising administering an effective amount a compound of Formula I and/or a pharmaceutically acceptable salt and/or solvate thereof to a subject in need thereof
wherein:
L is $C_{0-4}$alkylene;
$R^1$ is $C_{4-8}$cycloalkyl or $C_{4-8}$cycloalkene, each of which is unsubstituted or substituted with one or two substituents independently selected from $C_{1-4}$alkyl, $C_{1-4}$fluoroalkyl and $C_{1-4}$alkyl substituted with Cl or CN; and
$R^2$ is H, $NO_2$, Cl, F or CN.

7. The method of claim 6, wherein L is $CH_2$.

8. The method of claim 6, wherein the compound of Formula I is selected from

9. The method of claim 6, wherein the infection is an infection of a nematode of a species selected from *Cooperia oncophora, Haemonchus contortus*, and *Caenorhabditis elegans*.

10. The method claim 6, wherein the subject is selected from a human, a mammal, a bird, a plant, a seed, and soil.

11. The method of claim 10, wherein the subject is selected from a plant, a seed and soil and the composition is administered through one or more means selected from pre-planting, post-planting, as a feed additive, a drench, an external application, a pill and by injection.

12. The method of claim 1, wherein the infection is an infection of a nematode of a genus selected from *Ancylostoma, Dirofilaria, Toxocara, Ascaris, Uncinaria, Parascaris, Trichostrongylus, Oesophagostomum, Dictyocaulus, Cooperia* and *Haemonchus*.

13. The method of claim 12, wherein the infection is an infection of a nematode of a species selected from *Ancylostoma caninum, Dirofilaria immitis, Toxocara canis, Toxocara cati, Ascaris suum, Cooperia oncophora* and *Haemonchus contortus*.

14. The method of claim 1, wherein the subject is human.

15. The method of claim 1, wherein the subject is a domesticated animal.

16. The method of claim 6, wherein the infection is an infection of a nematode of a genus selected from *Ancylostoma, Dirofilaria, Toxocara, Ascaris, Uncinaria, Parascaris, Trichostrongylus, Oesophagostomum, Dictyocaulus, Cooperia* and *Haemonchus*.

17. The method of claim 16, wherein the infection is an infection of a nematode of a species selected from *Ancylostoma caninum, Dirofilaria immitis, Toxocara canis, Toxocara cati, Ascaris suum, Cooperia oncophora* and *Haemonchus contortus*.

18. The method of claim 6, wherein the subject is human.

19. The method of claim 6, wherein the subject is a domesticated animal or is livestock.

20. The method of claim 15, wherein the subject is livestock.

* * * * *